United States Patent [19]
Khanna et al.

[11] Patent Number: 6,132,748
[45] Date of Patent: Oct. 17, 2000

[54] METHOD FOR PRODUCING CHLORINE DIOXIDE USING ACIDIFIED EXPANDED AMORPHOUS ALUMINUM SILICATE IMPREGNATED WITH CHLORITE

[75] Inventors: Neeraj Khanna, Norman; Theodore D. Head, Noble; Bryan D. Lowery, Oklahoma City, all of Okla.

[73] Assignee: Bio-Cide International, Inc., Norman, Okla.

[21] Appl. No.: 09/251,051

[22] Filed: Feb. 18, 1999

Related U.S. Application Data

[60] Provisional application No. 60/075,289, Feb. 19, 1998.
[51] Int. Cl.⁷ .......................... A01N 25/00; A01N 59/08; A61K 33/14; A61K 9/00; A61K 9/01
[52] U.S. Cl. .................. 424/405; 252/187.21; 422/5; 422/37; 424/76.8; 424/661
[58] Field of Search ................... 424/405, 76.8, 424/661; 422/5, 37; 252/187.21

[56] References Cited

U.S. PATENT DOCUMENTS

| | | | |
|---|---|---|---|
| 4,547,381 | 10/1985 | Mason et al. | 426/316 |
| 4,689,169 | 8/1987 | Mason et al. | 252/186.24 |
| 5,695,814 | 12/1997 | Wellinghoff et al. | |
| 5,888,419 | 3/1999 | Casella et al. | 252/186.39 |

Primary Examiner—David M. Naff
Assistant Examiner—Deborah K. Ware
Attorney, Agent, or Firm—Bill D. McCarthy; Phillip L. Free, Jr.; Crowe & Dunlevy, P.C.

[57] ABSTRACT

An important and central aspect of the present invention is the use of expanded amorphous aluminum silicate (EAAS) as a vehicle for a chlorite salt. This vehicle, when exposed to moisture, will release chlorine dioxide ($ClO_2$) for purposes of deodorization or microbial suppression. Thus, where a particular area or volume is to be deodorized or made less microbally contaminated, the EAAS-chlorite salt (most preferably sodium chlorite) is placed in the area or volume to be treated and moisture is permitted to interact with the material. The result of the moisture is to permit the chemical reaction (presumably acidification) of the chlorite salt to yield chlorine dioxide gas. While normal EAAS has some inherent acidity, the inherent acidity is low enough so that, even when a chloride salt is encapsulated in the EAAS and the resultant mixture exposed to moisture, $ClO_2$ release is very slow and over an extended period. Under most conditions, a more rapid release of $ClO_2$ is desired for deodorization and/or sterilization. A more rapid release of chlorine dioxide may be accomplished by first treating the native EAAS with an acid, preferably a protic acid, to acidify chemical groups of the EAAS. After native EAAS is acidified and dried, if necessary, a chlorite salt such as sodium chlorite is incorporated therein.

11 Claims, 1 Drawing Sheet

METHOD FOR PRODUCING CHLORINE DIOXIDE USING ACIDIFIED EXPANDED AMORPHOUS ALUMINUM SILICATE IMPREGNATED WITH CHLORITE

RELATED APPLICATION

This application claims the benefit of U.S. Provisional patent application Ser. No. 60/075,289 entitled METHOD FOR PRODUCING CHLORINE DIOXIDE USING CHEMICALLY IMPREGNATED EXPANDED AMORPHOUS ALUMINUM SILICATE, filed Feb. 19, 1998, which is hereby incorporated by reference.

FIELD OF INVENTION

The present invention relates to a method for producing chlorine dioxide using expanded amorphous aluminum silicates ("EAAS") (CAS 93763-70-3).

BACKGROUND OF INVENTION

The present invention relates generally to a biocidal composition which releases chlorine dioxide for odor-diminishing biocidal or other purposes. The invention particularly relates to a composite formulated as a powder.

Chlorine dioxide ($ClO_2$) is a superior oxidizing agent widely used as a bleach, disinfectant, fumigant or deodorizer. It can penetrate the cell wall or membranes and cytoplasm of mold spores, bacteria and other microbiological contaminants at low concentrations.

The incorporation of chlorine dioxide or sodium chlorite in food packaging has prompted studies to determine whether residual levels of such preservatives result in a significant genetic or carcinogenic hazard to humans. Meier et al. studied the effect of subchronic and acute oral administration of chlorine, chlorine dioxide, sodium chlorite sodium chlorate and related substances on the induction of chromosomal aberrations and spermhead abnormalities in mice. Only the highly reactive hypochlorite resulted in a weak positive effect for mutagenic potential. The other compounds, including chlorine dioxide and sodium chlorite, failed to induce any chromosomal aberrations or increased numbers of micronuclei in the bone marrow of mice. Richardson et al. reported that an extensive study of the reaction of chlorine dioxide with water borne organics by the Environmental Protection Agency confirmed this observation.

Japanese Kokai Nos. 63/296,758, 63/274,434, and 57/168,977 describe deodorants containing chlorine dioxide incorporated in a polymer, ceramic beads, or calcium silicate wrapped in nonwoven cloth, respectively. Gels which generate chlorine dioxide for use as topical applications for disinfection are disclosed by Kenyon, et. al. Chlorine dioxide generating gels are generally formed by mixing a gel containing suspended sodium chlorite with a gel containing lactic acid immediately prior to use to avoid premature chlorine dioxide release. Chlorine dioxide releasing gels have also been used in food preservation.

Encapsulation processes have also been used in preparing sources of chlorine dioxide. Canadian Patent No. 959,238 describes generation of chlorine dioxide by separately encapsulating sodium chlorite and lactic acid in polyvinyl alcohol and mixing the capsules with water to produce chlorine dioxide.

Tice et al. describe gradual hydrolysis of alternating poly(vinyl methyl ether-maleic anhydride) or poly(lactic-glycolic acid) to generate acid which can release chlorine dioxide from sodium chlorite. A polyalcohol humectant and water are encapsulated with the polyanhydride or polyacid in a nylon coating. After sodium chlorite is diffused into the capsule through the nylon wall, an impermeable polystyrene layer is coacervated around the nylon capsule. Solvents are required for reaction and application of the capsules. The capsules can be coated onto surfaces to release chlorine dioxide. Although the capsules are said to provide biocidal action for several days to months, chlorine dioxide release begins immediately after the capsules are prepared. The batchwise process used to prepare the capsules also involves numerous chemical reactions and physical processes, some of which involve environmental disposal problems. Wellinghoff, et. al. describe methods of making a powdered biocidal composition for the release of $ClO_2$.

There is a need for a composite that can be easily activated to initiate chlorine dioxide release in use. A composition that is composed of and generates only FDA-approved substances, or those generally recognized as safe (GRAS), is particularly needed for food packaging and other applications where the substances can be ingested by or in contact with humans.

SUMMARY OF THE INVENTION

An important and central aspect of the present invention is the use of expanded amorphous aluminum silicate as a vehicle for a chlorite salt. This vehicle, when exposed to moisture, will release chlorine dioxide ($ClO_2$) for purposes of deodorization or microbial suppression. Thus, where a particular area or volume is to be deodorized or made less microbally contaminated, the EAAS-chlorite salt (most preferably sodium chlorite) is placed in the area or volume to be treated and moisture is permitted to interact with the material. The result of the moisture is to permit the chemical reaction (presumably acidification) of the chlorite salt to yield chlorine dioxide gas. While normal EAAS has some inherent acidity, the inherent acidity is low enough so that, even when a chlorite salt is encapsulated in the EAAS and the resultant mixture exposed to moisture, $ClO_2$ release is very slow and over an extended period. Under most conditions, a more rapid release of $ClO_2$ is desired for deodorization and/or sterilization. A more rapid release of chlorine dioxide may be accomplished by first treating the native EAAS with an acid, preferably a protic acid, to acidify chemical groups of the EAAS. After native EAAS is acidified and dried, if necessary, a chlorite salt such as sodium chlorite is incorporated therein.

In another embodiment of the present invention, the chlorite salt may be incorporated within the EAAS without prior acidification of the EAAS. In order to accelerate $ClO_2$ release, the EAAS-chlorite salt mixture may be exposed to a volatile acid such as acetic acid or the like. This may be prior to or in conjunction with the exposure of the EAAS incorporated chloride salt to moisture as found in water vapor or water droplets.

DETAILED DESCRIPTION OF THE INVENTION

Figure 1:
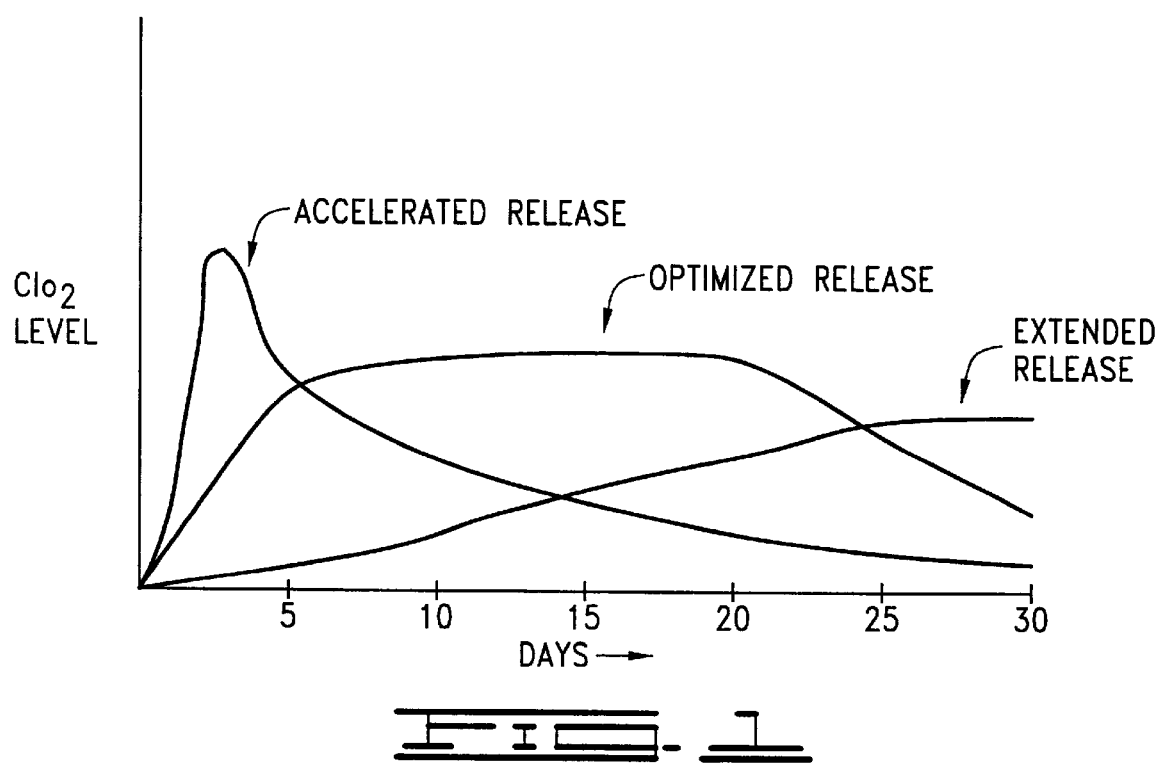
FIG. 1 shows $ClO_2$ release from accelerated release EAAS; optimized release EAAS; and extended release EAAS.

EAAS can be synthesized by heating naturally occurring siliceous volcanic rock, known as Perlite. Perlite ore is extracted in the U.S. and other countries, and is usually mined by scraping the earth's surface. Perlite is marketed by several companies, such as Incon Corporation of Media, Pa. and World Minerals, Inc. of Santa Barbara, Calif. The elemental analysis indicates that Perlite consists of 34% silicon and 7% aluminum and therefor falls under the category of A aluminum silicate minerals. Perlite is chemically inert and has the ability to expand in volume by an order of magnitude when heated to certain temperatures, hence the adjective "expanded". To expand the Perlite, the Perlite crude is first crushed to a particle size of approximately ⅝ inch in a primary crusher. The crushed Perlite is then passed through an oil-fired rotary dryer and then undergoes a secondary grinding to produce the desired particle size. The heating temperatures may range between 1400° and 2000° F., depending on water content and rate of heating. The word amorphous in EAAS is used to reflect the absence of definite crystalline structure.

One form of EAAS used for this invention is marketed by Paradigm International, Inc. of Irvine, Calif., under the brand name Stardust®. Another expanded Perlite product that is expected to behave similarly is Harbolit®, marketed by World Minerals Inc., of Santa Barbara, Calif. These products are moisturized forms of EAAS. Moisturization is performed to induce aggregates that preclude accidental inhalation.

The Moisturized EAAS is soaked with an aqueous solution of from about 0.01% to about 40% chlorite anion by weight. In particularly preferred embodiments the counterion is sodium, potassium or calcium, however any suitable source of the chlorite ion can readily be used in the alternative in accordance with the present invention. In a preferred embodiment, soaking may be achieved by spraying a 5% solution of sodium chlorite solution (such as ProOxine®, a product sold by BioCide International, Inc. of Norman, Okla.) while agitating the EAAS mechanically. The soaked EAAS is then dried at a temperature of 120° C. for about two hours and sealed in an air-tight container or desiccator to prevent moisture absorption.

The activator is prepared in a similar manner by soaking EAAS in a protic acid solution. Any suitable protic acid may be used such as, without limitation, phosphoric, hydrochloric, sulphuric, nitric, acetic, citric, tartaric, glycolic, mandelic, salicylic, malic, maleic, aspartic, lactic, or other structurally similar acids. Persons skilled in the art will recognize other suitable protic acids, all of which are intended to be suitable for use in the present invention. The concentration of the soaking solution can range from about 0.01 M to saturated, depending on the desired potency of the activator.

The chlorite impregnated EAAS and the acid impregnated EAAS can be combined in a specific ratio to release a desired concentration of chlorine dioxide. A most preferred embodiment is to first acidify EAAS, and then incorporate a chlorite salt into the acidified EAAS. In a particularly preferred embodiment, the mixture is packaged in a spin bonded olefin bag, such as a Tyvek® bag, of appropriate porosity. Such bags are composed of porous material that allows moisture to diffuse into the bag, yet is able to retain the EAAS materials inside the bag. Upon contact with moisture, the mixture releases $ClO_2$. Bags are best sealed from moisture until production of $ClO_2$ is desired, such as in a sealed plastic bag. In certain uses, the chlorite-impregnated EAAS and the acid impregnated EAAS can also be mixed on site to produce $ClO_2$, as opposed to premixing of the ingredients. Other suitable applications for the present invention will be readily recognized by those skilled in the art, all of which are within the spirit and scope of the present invention. For instance, in an alternative embodiment a push/pull bottle can be used to store and activate the dry, chemically impregnated ingredients.

Although the invention is not limited by a particular mechanism, a likely mechanism of $ClO_2$ release may be explained as follows. The water molecules in the moisture provide the medium that facilitates the interaction of chlorite ions with the protons. The chlorite ions then probably reacts with the protons according to the following equation.

$$5ClO_2^- + 4H^+ \rightarrow 4ClO_2 (g) + Cl^- + 2H_2O$$

One advantage of the present invention is the moisture-induced solid phase release of $ClO_2$ that creates an antimicrobial and deodorizing atmosphere at the site of application. In low ambient moisture environments, moisture can be fogged or otherwise applied from outside to accelerate $ClO_2$ production; however, typically normal humidity will supply the necessary moisture. The amorphous nature of the supporting phase, provides a much longer time-range for sustained release of $ClO_2$ as compared to a support that is homogeneous in nature. This occurs due to the existence of a range of pore sizes ($\approx 10$ to $\approx 100$ Å) in the amorphous substance that expands the kinetic time scale for the penetration of the water molecules.

The product may be used for the microbial control of dry or semi dry goods such as produce, cosmetics, medical devices, paper fabric, and fertilizers and other agricultural items. This product can be used for odor control, since $ClO_2$ has been shown to exhibit excellent deodorizing properties.

EXAMPLE 1

One preferred embodiment is described as follows: EAAS is soaked with a protic acid. The amount of protic acid is in the range of 5 to 100% of the weight of EAAS. The exact quantity depends on the type of acid and the desired characteristics of the final product. In general, three different types of products can be manufactured. These are i) accelerated release, ii) optimized release and iii) extended release. The $ClO_2$ release profiles for these products are shown in FIG. 1. To make product that will provide accelerated release, a greater amount of acid will be added. On the other hand, to make product that will provide optimized release, a lesser amount of acid will be added. On the other hand, to make product that will provide extended release, comparatively lower amounts or no acid may be added.

After soaking with acid, EAAS is baked in the oven at a temperature between 80° C. and 300° C. for several hours. The optimum temperature and time for baking is approximately 150° C. and two hours, respectively. The temperature condition can be varied to produce different types of products. For example, lower temperatures ($\approx 100°$ C.) and short baking times (under 30 minutes) will produce product that will demonstrate accelerated release.

Subsequent to baking, solid sodium chlorite is added to EAAS. The weight of sodium chlorite can range from 1 to 100% of the weight of EAAS. The weight of sodium chlorite is added to the EAAS depends on the desired characteristics of the product. In certain preferred embodiments, the quantity of sodium chlorite added to EAAS is between 4 to 15 %. Thus the amount of acid, strength of acid and baking time are single variables to produce desired patterns or $ClO_2$ release. Of course the concentration and type of chlorite incorporated into the native or acid-treated EAAS may also be varied to produce desired $ClO_2$ release patterns.

The most commonly available form of sodium chlorite is its 80% pure form. One of the sources for this product is Vulcan Chemicals, Birmingham, Ala. Other sources and other purities of the preferred $NaClO_2$ may be used.

The EAAS used in the following examples was obtained from two different sources; 1) Paradigm International, Inc., CA and ii) Aldrich Chemical Company, Milwaukee, Wis. These two materials are subsequently P1 and P2, respectively. The density of P2 is much higher than that of P1.

To monitor the level of free $ClO_2$ produced from the EAAS product, gallon jars made of poly(ethyleneterephthalate) commonly known as PET may be used. The EAAS product was packaged and used in a 50 cc widemouth bottle is made of high density polyethylene (HDPE). The cap on the bottle had a push-pull mechanism for sealing or allowing the diffusion of air with the environment via an opening of 0.8 cm diameter. The $ClO_2$ gas that is generated by the product is discharged into the environment through this opening.

To measure the concentration of $ClO_2$ released from the EAAS product, the bottle was kept in the PET jar with a closed lid for a definite period of time and the $ClO_2$ levels were measured with a $ClO_2$-monitoring device known as Tox-Array 1000 which is manufactured by Mil-Ram Technologies, Inc., San Jose, Calif. This device was calibrated to measure from 0.1 to 20 ppm of $ClO_2$. For each measurement the sample was drawn from the top of the jar by opening the lid slightly and allowing the insertion of the sample suction tube into the jar. The suction tube was directly connected to the monitoring device.

The concentration of total available $ClO_2$ was measured by iodometric method 4500-$ClO_2$ B, as described in the standard methods (19th Edition) of American Water Works Association.

The jars were kept in the ambient lab environment and the inside temperature was monitored. The temperature was between 20° C. and 25° C. The humidity of the inside of these jars was maintained between 80% and 95% RH by spraying calculated amounts of water in the jars. The humidity was monitored with a hygrometer manufactured by Radio Shack (model 63-867A).

EXAMPLE 2

230 mL of 0.6 M hydrochloric acid was sprayed on each of the 230 g of P1 and P2. These substances were sprayed with a generic spray bottle, with thorough stirring between every few squirts. The acidified EAAS was allowed to bake at 250° C. for one hour. The EAAS turned slightly brown in color. This may be due to oxidation of $Fe^{2+}$ to $Fe^{3+}$.

Two bottles of each P1 and P2 were kept in three different locations for trials for odor removal. The results are reported in Tables 1 and 2. Samples A and B were kept in a toilet facility (100 sq. ft.), samples B and C were kept in the laboratory (1,600 sq. ft.), and sample E and F were kept in an office (1,500 sq. ft.).

TABLE 1

Product made from P1
Free $ClO_2$ (ppm)

| Day | Incubation Time | Sample A | Sample B | Sample C | Sample D | Sample E | Sample F |
|---|---|---|---|---|---|---|---|
| 0 | 15 min | 6.4 | 6.5 | 6.5 | 6.6 | 6.4 | 6.5 |
| 1 | 15 min | 0.4 | 0.7 | 1.3 | 1.2 | 1.1 | 1.8 |
| 5 | 4 hours | 5.0 | 4.8 | 5.2 | 5.3 | 4.8 | 4.7 |
| 6 | 4 hours | 2.1 | 2.0 | 2.1 | 2.1 | 1.0 | 2.1 |
| 7 | 4 hours | 2.2 | 2.8 | 2.5 | 2.3 | 1.3 | 2.8 |
| 8 | 4 hours | 1.3 | 1.5 | 1.3 | 1.0 | 0.5 | 1.3 |

TABLE 1-continued

Product made from P1
Free $ClO_2$ (ppm)

| Day | Incubation Time | Sample A | Sample B | Sample C | Sample D | Sample E | Sample F |
|---|---|---|---|---|---|---|---|
| 11 | 4 hours | 1.2 | 2.5 | 1.5 | 1.0 | 0.3 | 1.2 |
| 12 | 4 hours | 1.5 | 2.4 | 1.7 | 1.8 | 0.5 | 1.3 |
| 13 | 4 hours | 1.2 | 1.9 | 1.4 | 1.4 | 0.6 | 1.1 |
| 14 | 4 hours | 3.1 | 3.2 | 2.1 | 2.3 | 0.4 | 1.4 |
| 15 | 4 hours | 2.3 | 2.8 | 2.2 | 2.3 | 0.7 | 0.8 |
| 18 | 4 hours | 1.6 | 1.7 | 0.5 | 1.1 | 0.7 | 0.1 |
| 19 | 4 hours | 2.1 | 2.0 | 1.1 | 1.8 | 0.9 | 0.2 |
| 21 | 4 hours | 2.0 | 2.4 | 1.0 | 2.0 | 1.2 | 0.5 |
| 22 | 4 hours | 1.8 | 1.9 | 1.0 | 1.8 | 0.8 | 0.3 |

TABLE 2

Product made from P2
Free $ClO_2$ (ppm)

| Day | Incubation Time | Sample A | Sample B | Sample C | Sample D | Sample E | Sample F |
|---|---|---|---|---|---|---|---|
| 0 | 15 min | 9.8 | 9.9 | 9.7 | 9.9 | 9.8 | 9.8 |
| 1 | 15 min | 2.7 | 3.5 | 3.3 | 3.2 | 2.6 | 3.1 |
| 4 | 15 min | 0.3 | 0.9 | 0.8 | 0.8 | 1.0 | 0.9 |
| 5 | 1 hour | 4.3 | 4.0 | 3.0 | 3.3 | 2.3 | 3.0 |
| 6 | 1 hour | 0.9 | 2.1 | 1.5 | 1.4 | 1.1 | 1.5 |
| 7 | 1 hour | 0.9 | 2.0 | 1.4 | 1.3 | 0.5 | 1.2 |
| 8 | 1 hour | 0.5 | 1.4 | 1.4 | 0.5 | 0.4 | 0.7 |
| 11 | 1 hour | 0.4 | 1.2 | 0.9 | 1.0 | 0.3 | 0.7 |
| 12 | 1 hour | 0.8 | 1.5 | 1.2 | 1.1 | 0.6 | 1.1 |
| 13 | 1 hour | 1.1 | 1.5 | 0.8 | 0.7 | 0.3 | 1.1 |
| 14 | 1 hour | 3.3 | 3.2 | 2.0 | 1.8 | 0.9 | 1.6 |
| 15 | 1 hour | 4.1 | 3.1 | 1.6 | 1.4 | 0.4 | 0.6 |
| 18 | 1 hour | 3.8 | 3.5 | 0.7 | 1.3 | 0.9 | 0.7 |
| 19 | 1 hour | 5.1 | 4.9 | 1.5 | 2.1 | 2.3 | 1.7 |
| 21 | 1 hour | 3.9 | 4.8 | 3.0 | 3.5 | 3.1 | 1.1 |
| 22 | 1 hour | 2.5 | 3.6 | 2.1 | 2.5 | 1.9 | 0.9 |

EXAMPLE 3

Mencaptoethanol is a fundamental molecule that is one cause for odors from rotten food substances. We tested the effect of our product in eliminating the odor caused by this chemical substance. $25\mu$ of 1-mercaptoethanol (Aldrich) was placed in each of two PET jars of the type described above. In the first jar, a bottle containing 5 g of P1. was placed. The second jar was treated as control, and no product was placed in it. The lids were placed back on both jars. After 12 hours, the product bottle was taken out and the jars aired for 30 minutes. Subsequently, they were tested for mercaptan odor by 5 different individuals. None of them could detect any odor in the first jar, whereas the control-jar had strong odor of the mercaptan. The mechanism for the odor removal is believed to be the oxidation of the mercaptan by $ClO_2$.

EXAMPLE 4

This product is very effective in removing onion odors. 25 g of chopped white onions were stored in two PET jars overnight. The onions were removed the next day and the bottle with P1 product was placed in one of the jars. After 12 hours, the jars were inspected for odor by 5 different individuals. It was agreed that the odor was eliminated from the jar that was treated with the P1 product.

EXAMPLE 5

Four samples, each containing 5 g of P1, were treated with 0.5 mL, 1 mL, 3 mL and 5 mL of 0.6 M HCl. Similarly, four examples each containing 10 g of P2, were treated with 0.5 mL, 1 mL, 3 mL and 5 mL of 0.6 M HCl. These samples were allowed to air dry on the laboratory bench, and after one week. 0.5 g $NaClO_2$ was added to them. These samples were packaged in the 50 cc bottles described in a prior Example. The $ClO_2$ levels were monitored in the similar manner as mentioned in earlier examples. In these cases the characteristics of $ClO_2$ release matched that of accelerated release as shown in FIG. 1. The results are presented in Tables 3 and 4.

TABLE 3

Product made from P1
Free $ClO_2$ (ppm)

| Day | Incubation Time | 0.5 mL Acid | 1 mL Acid | 3 mL Acid | 5 mL Acid |
| --- | --- | --- | --- | --- | --- |
| 0 | 1 hour | 4.5 | 6.8 | 7.3 | 4.2 |
| 1 | 1 hour | 0.4 | — | — | — |
| 2 | 1 hour | 0.0 | 1.8 | — | — |
| 3 | 1 hour | — | — | 0.0 | — |
| 5 | 1 hour | — | 5.6 | — | — |
| 6 | 1 hour | — | 0.0 | — | 0.0 |

TABLE 4

Product made from P2
Free $ClO_2$ (ppm)

| Day | Incubation Time | 0.5 mL Acid | 1 mL Acid | 3 mL Acid | 5 mL Acid |
| --- | --- | --- | --- | --- | --- |
| 0 | 1 hour | 7.6 | 1.0 | 11.2 | 10.6 |
| 1 | 1 hour | 2.4 | 9.3 | — | — |
| 2 | 1 hour | — | 3.4 | — | — |
| 3 | 1 hour | — | — | 1.2 | — |
| 4 | 1 hour | — | — | — | — |
| 5 | 1 hour | 0.0 | 0.4 | — | — |
| 6 | 1 hour | — | 0.1 | — | — |

EXAMPLE 6

In this example, $NaClO_2$ is mixed with P1 and P2 that were not treated with any acid. The ratio of mixing was 0.5 g $NaClO_2$:5 g P1 and 0.5 g $NaClO_2$:10 g P2. these cases the characteristics of $ClO_2$ release matched those of extended release as FIG. 1. The $ClO_2$ level released from the 50 cc bottle (described in Example 1) were below the detection limit of the Tox-Array monitoring device. However, when bulk amounts of both P1 and P2 formulations were left in the PET jars for approximately 1½ months, ≈10 ppm and ≈6 ppm of $ClO_2$ was detected, respectively.

The following references as well as those separately cited above are incorporated in pertinent part by reference herein for the reasons cited.

References:

1) Greenwood, 'N. N. Eamshaw, A. In Chemistry of the Elements; Pergamon Press: New York, 1989, pp399–416.

2) Perlite Institute Inc., 88 New Drop Plaza, Staten Island, N.Y. 10306-2994.

3) Masschelein, W. J. In Chlorine Dioxide, Chemistry and Environmental Impact of Oxychlorine Compounds; Ann Arbor Science: Ann Arbor, 1979.

4) Wellinghoff, et. al., U.S. Pat. No. 5,695,814.

5) Tice, et al., U.S. Pat. No. 4,585,482.

6) Meier, et al., Environ. Mutagenesis, 7, 201 (1985).

7) Richardson, et al., Environ. Sci. Technol., 28, 592 (1994).

8) Kenyon et al., Am. J. Vet. Res., 45(5), 1101 (1986).

That what is claimed:

1. A method for treating an area with $ClO_2$ for microbial and odor control, the method comprising placing in the area an acidified Expanded Amorphous Aluminum Silicate (EAAS) impregnated with a chlorite salt packaged in a bag; and diffusing moisture into the bag sufficient to generate $ClO_2$ to treat said area.

2. A method for producing a source of $ClO_2$, the method comprising:

treating Expanded Amorphous Aluminum Silicate (EAAS) with an acid;

drying the acidified EAAS; and incorporating a chlorite salt into the dried acidified EAAS and packaging the resultant chlorite salt containing dried acidified EAAS in a spin bonded olefin bag.

3. The method of claim 2, wherein treating with acid comprises.:

providing a solution of protic acid; and soaking the EAAS in the solution of protic acid.

4. The method of claim 3, wherein the solution of protic acid contains a concentration of protic acid from 0.01 M to saturation.

5. The method of claim 2, wherein drying comprises heating the acidified EAAS at a temperature of 120° C. for approximately two hours.

6. The method of claim 2, wherein the incorporating of chlorite salt comprises soaking the EAAS in an aqueous solution of from about 0.01 percent to about 40 percent chlorite anion.

7. A composition of matter comprising an acidified Expanded Amorphous Aluminum Silicate (EAAS) containing a chlorite salt and packaged in a spin bonded olefin bag.

8. The composition of claim 7 wherein the chlorite salt is sodium chloride.

9. The composition of matter of claim 7 defined further as being substantially anhydrous.

10. A method for producing a source of $ClO_2$, the method comprising:

impregnating Expanded Amorphous Aluminum Silicate (EAAS) with a chlorite salt to produce a chlorite impregnated EAAS;

impregnating EAAS with an acid to produce an acid impregnated EAAS;

combining the chlorite impregnated EAAS with the acid impregnated EAAS, to form a mixture packaging the mixture in a bag.

11. The method of claim 10, wherein impregnating the EAAS with chlorite salt comprises:

spraying a five percent solution of sodium chlorite solution onto the EAAS; and simultaneously agitating the EAAS.

* * * * *

UNITED STATES PATENT AND TRADEMARK OFFICE
CERTIFICATE OF CORRECTION

PATENT NO. : 6,132,748
DATED : October 17, 2000
INVENTOR(S) : Neeraj Khanna, Theordore D. Head and Bryan D. Lowery It is certified that error appears in the above-identified patent and that said Letters Patent is hereby corrected as shown below:

Column 3,
Line 5, replace "of A aluminum" with -- of aluminum --
Line 20, replace "Harbolit®" with -- Harbolite® --

Column 4,
Line 21, replace "($\approx$ 10 to $\approx$ 100Å)" with -- (~ 10 to ~100Å) --
Line 50, replace "($\approx$ 100°C)" with -- (~100°C) --

Column 7,
Line 44, replace "P2. these" with -- P2. In these --
Line 46, replace "release as FIG. 1." with -- release as shown in figure 1. --
Line 50, replace "$\approx$10 ppm and $\approx$6" with -- ~10 ppm and ~6 --

Column 8,
Line 55, replace "form a mixture packaging" with -- form a mixture; and packaging --

Signed and Sealed this

Fourth Day of January, 2003

JAMES E. ROGAN
*Director of the United States Patent and Trademark Office*